United States Patent [19]

Orlowski et al.

[11] 4,380,432
[45] Apr. 19, 1983

[54] METHOD FOR ADHERING STRUCTURES TO TEETH

[75] Inventors: Jan A. Orlowski, Altadena; David V. Butler, West Covina, both of Calif.

[73] Assignees: Scientific Pharmaceuticals, Duarte, Calif.; Sankin Industries, Ltd., Tokyo, Japan

[21] Appl. No.: 183,743

[22] Filed: Sep. 3, 1980

[51] Int. Cl.³ .............................................. A61K 6/08
[52] U.S. Cl. ..................................... 433/9; 433/180; 433/219; 523/118
[58] Field of Search ................... 433/9, 180, 183, 219, 433/8; 523/118

[56] References Cited

U.S. PATENT DOCUMENTS

| | | | |
|---|---|---|---|
| 2,569,767 | 10/1951 | Knock | 433/199 |
| 3,179,623 | 4/1965 | Bowen | 260/47 |
| 3,541,068 | 11/1970 | Taylor | 260/42.52 |
| 3,629,187 | 12/1971 | Waller | 260/42.52 |
| 3,766,132 | 10/1973 | Lee et al. | 260/41 |
| 3,926,906 | 12/1975 | Lee et al. | 260/42.53 |
| 4,102,856 | 7/1978 | Lee et al. | 260/42.53 |
| 4,107,845 | 8/1978 | Lee et al. | 260/42.17 |
| 4,131,729 | 12/1978 | Schmitt et al. | 526/282 |
| 4,172,323 | 10/1979 | Orlowski | 264/16 |
| 4,200,980 | 5/1980 | Johnston | 433/228 |

Primary Examiner—Lorenzo B. Hayes
Attorney, Agent, or Firm—Cushman, Darby & Cushman

[57] ABSTRACT

Adhesives and methods are provided for fixed prosthesis by bonding a pontic to abutment teeth. The adhesive is preferably a methacrylate based resin adhesive comprising 2.5-30% of an elastomer which is a polymer of a substituted or unsubstituted butadiene monomer. A preferred etchant for preparing the abutment for adhesive bonding is 2-15% HCl. The prosthesis technique does not irreversibly affect the abutment teeth. The preferred adhesive may also be used for immobilizing injured or periodontically affected teeth or for stabilizing teeth in order to retain the results of orthodontic treatment.

19 Claims, 3 Drawing Figures

METHOD FOR ADHERING STRUCTURES TO TEETH

BACKGROUND OF THE INVENTION

The advent of acid etching techniques in dentistry has opened new alternatives to existing methods in the field of dental prosthesis. The promise of securing the pontic in place with adhesive forces rather than by the means of mechanical retention appeared to offer some significant advantages over both fixed and removable dental prosthesis. The fixed prosthesis technique requires irreversible operational preparation of the abutment teeth involving destruction of tooth enamel. The fixed prosthesis techniques are also very costly and require a significant time involvement on the part of the patient, dentist and technician. The incidents of postoperational abutment teeth sensitivity, loss of their vitality and incidents of caries developing under cemented dentine are not infrequent consequences of fixed bridge preparations.

Removable prosthetic appliances are even more objectionable. For instance, they are generally functionally and esthetically inferior, uncomfortable and cause damage to the supporting teeth. Their use impairs oral hygiene and their safety is questionable.

An adhesive technique that relies on bonding of self-cured acrylic resin to phosphoric acid etched tooth enamel could provide a conservative, inexpensive, painless and comfortable solution for making partial dentures. Moreover, the same technique appeared to be promising for wireless stabilizing of teeth, for example, in periodontic or post-orthodontic treatment.

Attempts to make an adhesive pontic utilizing acid etching techniques were rewarded, however, with a limited success. One of the possible reasons for these failures was inadequacy of the adhesive. With the exception of the materials described in U.S. Pat. No. 4,172,323, materials specifically used for bonding pontics were not developed and, therefore, not suitable for this particular purpose.

In the reported clinical cases, a common composite restorative material or system comprised of composite restorative and liquid sealer was used in conjunction with phosphoric acid etching solutions. Note, for example the following publications:

(1) Leonard L. Portnoy, "Construction A Composite Pontic in a Single Visit", Dental Survey, August, 1973, pp. 20–23;
(2) Sherwood S. Tucker, "Repair of a Loosened Pontic Replaced by Acid Etching", Dental Survey, July, 1974, p. 44;
(3) Susan A. McEvoy and John R. Mink, "Acid-Etched Resin Splint for Temporarily Stabilizing Anterior Teeth", Journal of Dentistry for Children, November-December, 1974, pp. 439–41;
(4) Paul M. Lambert, David L. Moore and Harry H. Elletson, "In Vitro Retentive Strength of Fixed Bridges Constructed with Acrylic Pontics and An Ultraviolet-light Polymerized Resin", J.A.D.A., Vol. 92, April, 1976, pp. 740–43;
(5) Robert L. Ibsen, "Fixed Prosthetics with a Natural Crown Pontic Using an Adhesive Composite.", J.S.C.D.A., Vol. 41, 1974, pp. 100–102;
(6) Richard I. Vogel, "The Use of a Self-Polymerizing Resin with Enamel Etchant for Temporary Stabilization", J. Periodontal., February, 1976, pp. 69–71;
(7) A. Stuart, "An Unusual Space Maintainer Retained by an Acid-Etched Polymer Resin", British Dental Journal, Dec. 3, 1974, pp. 437–38;
(8) Lee Pharmaceuticals Technical Bulletin #9090-1 (by Jan A. Orlowski and Robert Elwell), "Use of Restodent Dental Restorative in Fixed Bridge Prosthesis as a Long Term Temporary Space Maintainer", Apr. 20, 1973;
(9) Abraham M. Speiser, "Transitional Splinting with Adhesive Material", Journal of the New Jersey Dental Association, February, 1974, pp. 34–35.

The entire disclosures of these publications are incorporated herein by reference and relied upon.

In these clinical cases, the etching procedure remained the same as used for restorative applications that are much less demanding when it comes to bonding strength. Moreover, the composite restorative materials lack flexibility and crack resistance, the characteristics most desirable for an adhesive used for bonding the pontic. During chewing, the teeth move in relation to each other. This imposes the requirement of flexibility, and fatigue resistance on the material used as an adhesive, making the ordinary restoratives unsuitable for this purpose.

U.S. Pat. No. 4,172,323, the entire disclosure of which is incorporated herein by reference and relied upon, describes a system for bonding pontics to the abutment teeth using a plastic screen in order to increase the force required to dislodge it. A methacrylate self-cured type adhesive of a non-composite type used in this system had the ability to bond to the reinforcing screen. The increase in the bonding strength achieved by the use of the screen was significant. However, it was not necessarily sufficient especially for posterior pontics. Moreover, it should be remembered that the reason for failures in adhesive type pontics is not necessarily insufficient bonding strength to etched enamel but most often inadequate mechanical properties of the adhesive material and its limited chemical resistance to the oral environment. It appears that in those respects the discussed patent offered little improvement over the prior art.

Bonding to human enamel relies on a number of tiny tags of cured adhesive extending into the crevices of etched enamel surface. Taking into consideration the uneven distribution of stresses during chewing and jaw movement, the properties of the adhesive such as flexural strength, impact resistance and elasticity become of prime importance, especially for posterior pontics where greater movements and greater mastication forces are involved. Highly cross-linked methacrylate type resins constituting the backbone of the adhesives used for bonding pontics were generally too stiff and too brittle for these applications. The chemical resistance to oral fluids was another important factor at least with some of these adhesive materials.

SUMMARY OF THE INVENTION

One aspect of the present invention relates to a methacrylate based dental adhesive comprising from about 2.5% to about 30% by weight of elastomer. This elastomer may be a homopolymer or copolymer of at least one conjugated diene monomer containing 4 to 10 carbon atoms.

Another aspect of the invention relates to a method for mounting a dental article such as a pontic in the mouth by bonding this article to abutment teeth with the preferred adhesive of the present invention.

A further aspect of the invention relates to the preparation of abutment teeth for adhesive bonding by etching these teeth with a 2-15% hydrochloric acid solution for 30-300 seconds.

DETAILED DESCRIPTION OF THE INVENTION

Figure 1:
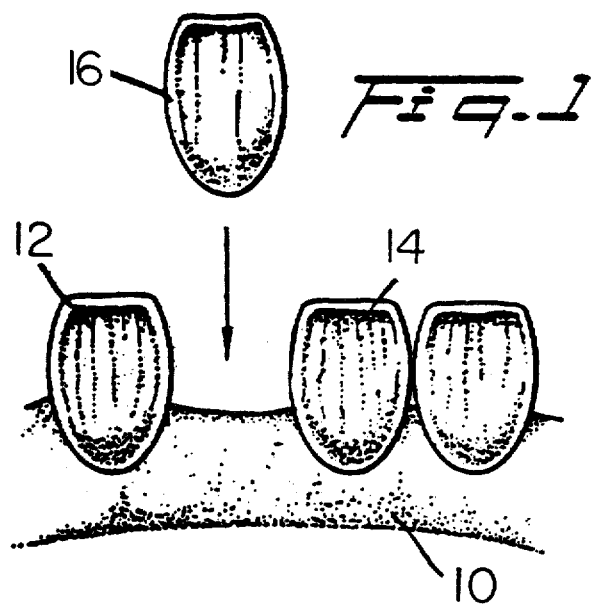
FIG. 1 is a fragmentary view, in elevation, of a human lower jaw (seen from the inside) from which one tooth, such as a lateral incisor, is missing, with a pontic shown above the vacant space, the pontic being of a shape and size suitable for installation as a part of a fixed bridge.

While certain aspects of the invention are illustrated in the drawing by application to the securing of a pontic in place to form a fixed bridge, the invention is equally applicable to securing larger items in place, such as, for example, a bridge made of two artificial pontics molded together or, alternatively, bonded together in accordance with the present invention, and the invention is equally applicable to splinting, where the pontic is set in the gum. One caveat is that the support surfaces in the mouth, to which the adhesive bond is to be made, must be free of gold or amalgam restorations, that is, suitable surfaces must be available for bonding.

To make a fixed bridge from a single pontic, in accordance with the present invention, the following general technique can be followed, with reference to the drawing by numerals of reference.

Figure 2:
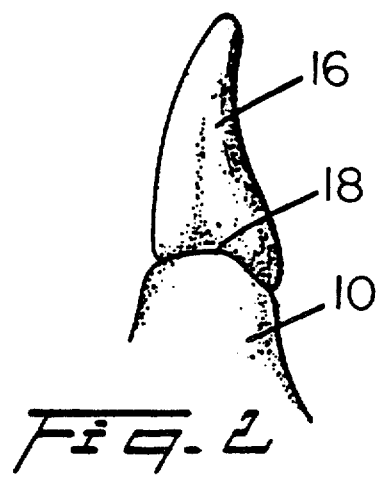
FIG. 2 is a fragmentary side elevation view of an artificial pontic seated on the gum, to replace a missing tooth, showing how the pontic can be shaped to seat lightly on the gum.
Figure 3:
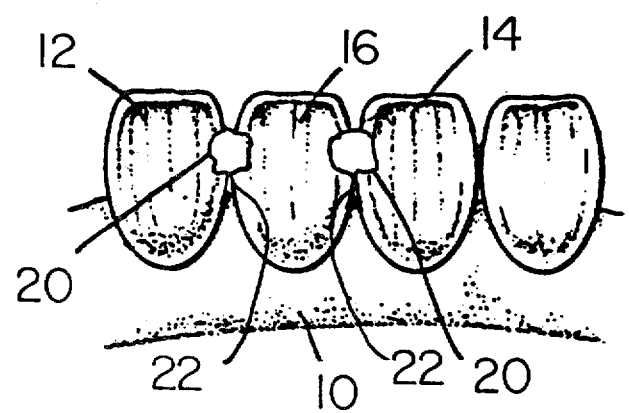
FIG. 3 is a fragmentary elevation of the human lower jaw shown in FIG. 1, again from the lingual side, with the pontic adhesively secured in place in accordance with one embodiment of this invention.

First, an impression is taken of the jaw from which the tooth is missing, and a pontic is obtained. The pontic is shaped to fit the model. The impression would be taken of the lower jaw 10 and would show the two natural abutment teeth 12 and 14, having a vacant space between them. The pontic 16 would be shaped to fit this vacancy and its size would be such as to permit minimal clearance with the confronting surfaces of the natural abutment teeth 12 and 14. The lower face 18 of the pontic would be shaped as shown in FIG. 2, to rest lightly on the gum of the lower jaw 10.

When the fixed bridge is to be installed, an optional step may be taken to improve the mechanical bond. In many cases, this optional step is not necessary, particularly where only a single pontic bridge is to be installed, and therefore this step is not shown in the drawing. This optional step consists of making mechanical undercuts or grooves in the pontic to assist in retention and further resist shear forces. The preferred form for these optional undercuts and grooves is achieved by cutting a series of lingual grooves from mesial to distal with a coarse fissure burr across the lingual surface. One or two coarse undercuts may be made on each proximal surface of the pontic. Any roughened material should be left in place, further to assist in retention, but any loose material should be dressed away. The surfaces of the grooves should be left as coarse as possible.

Next, the contact areas of the proximal surfaces of the abutment teeth may be dressed with a coarse diamond or a coarse garnet, so as to remove plaque, cuticle, protein, weak enamel, and the like. Optionally, although not preferably, small undercuts in the enamel may be made in the contact area, also for the purpose of increasing the area available for bonding and the resistance to shear forces.

The bridge area is then isolated with cotton rolls, and a chemical etching agent is applied to support surface areas of the abutment teeth. Suitable etching agents are well known and include acidic etchants such as solutions of phosphoric acid and citric acid, as well as alkaline etchants. However, it has been discovered that 2-15% hydrochloric acid solution is a preferred etchant.

After e.g., two to three minutes, the etching agent is rinsed off with water and dried.

After etching, washing, and drying, a dry field is maintained, either by air or by the use of a dental drying agent such as, for example, a mixture of equal parts of acetone and diethyl ether, or one of the other drying solutions disclosed in U.S. Pat. No. 3,905,110 the entire disclosure of which is incorporated herein by reference and relied upon. The appropriate surface areas of the pontic are also kept dry. Removal of all moisture is desirable since it has a deleterious effect upon many dental adhesives.

Once the bonding surfaces of the abutment teeth and of the pontic have been etched, washed, and dried, they should not be touched with either fingers or instruments. Similarly, the patient should not be permitted to cause the treated areas to become moist with saliva, since this could cause the adhesive bond to be inadequate.

At this point, a layer 20 of the adhesive is applied on each support surface of the abutment teeth. Adhesive is also applied to the pontic, and the pontic is then placed in position and held without stress until initial set occurs, which may take place, e.g., within two to three minutes. In applying the adhesive, if grooves and undercuts have been employed, they should be completely filled with the adhesive.

The pontic may be either an acrylic artificial pontic, or a pontic made of some other satisfactory polymeric material, preferably one that is at at least partially soluble in the liquid binder of the adhesive composition, or it may be the patient's natural tooth or crown. When a natural tooth is used, it may be set in the gum, in the known fashion for splinting. When the patient's crown is used, the excess root is cut off and the crown is dressed to the desired dimensions. The roots are cleansed and obturated by injecting a suitable adhesive. The crown can then be treated in the same way that an artificial pontic would be treated.

In making a fixed bridge, the preferred pontic for use is one formed of an acrylic plastic. However, a pontic formed of porcelain or a natural tooth may also be employed. In addition, a composite restorative molded tooth, or a tooth made from any suitable substrate having an acrylic or porcelain veneer or facing, may be employed. Preferably, the pontic is either an acrylic plastic tooth or a tooth that is faced or veneered with acrylic plastic.

Gaps 22 should be provided to permit the patient to floss in this area after the adhesive hardens. This flossing may be accomplished by means of floss threaders as described on page 438 of A. Stuart, "An Unusual Space Maintainer Retained by an Acid-Etched Polymer Resin", *British Dental Journal*, Dec. 3, 1974, pp. 437–38. Where appropriate in certain adhesive applications, wooden interdental spacers may be used to limit the flow of resin into these gaps in the manner discussed in Richard I. Vogel, "The Use of a Self-Polymerizing Resin with Enamel Etchant for Temporary Stabilization", *J. Periodontal*, February, 1976, pp. 69–71. Once initial set has occurred, additional adhesive can be added, to increase the area of the bond, although usually added adhesive is not necessary. The adhesive should be permitted to cure for at least twenty to thirty minutes, before any stress is applied to the pontic. At the end of a reasonable cure time without the application of stress, the excess adhesive can be removed to establish proper embrasures and to produce the desired cosmetic appearance.

When a 2–15% aqueous hydrochloric acid solution is used as the etchant, the adhesive may be any suitable high bonding strength dental adhesive, including many of the formulations used in dental composite restoratives, one qualification upon this being that any inorganic filler present should be limited in quantity to not more than 60% by weight of the adhesive composition and preferably less. Indeed, it is contemplated that no fillers may be used, or that particulate precured polymers may be employed that are sufficiently compatible with the liquid binder of the adhesive so that upon cure a monolithic or integral mass is obtained. In any case, the adhesive that is selected must readily wet the surfaces of the pontic and of the abutment teeth to be suitable.

The adhesive preferably contains 2.5–30% by weight of an elastomeric material derived from one or more conjugated diene monomers containing 4 to 10 carbon atoms. When such an elastomer containing adhesive is used, any suitable etchant may be used. However, it is preferred to use the above-mentioned hydrochloric acid etchant along with the above-mentioned elastomer containing adhesive.

The adhesive composition should preferably have a curable liquid portion which readily wets the surfaces of the pontic and of the abutment teeth, and also has the ability to penetrate into the etched tooth surfaces and into the pontic. The end product of this preferred embodiment is a bond wherein the adhesive is cured not only on the surfaces of the abutment teeth but also where it penetrates into these surfaces in "tags" that may be many microns long, and that may penetrate a compatible pontic to a depth of a millimeter or more. While the adhesive composition need not contain any filler, various amounts and types of fillers may also be included.

The preferred adhesive may be characterized as a methacrylate based adhesive. In other words, the curable portion of the adhesive should include predominantly monomers or prepolymers (e.g., dimers or trimers of such monomers) which have one or more methacrylate moieties. Preferably, the dental adhesive comprises from about 40% to about 95% by weight of a methacrylic monomer or a mixture of methacrylic monomers. Such monomers include monofunctional methacrylates, which have one methacrylate moiety per molecule, such as methacrylic acid, lower alkyl methacrylates (e.g., where alkyl have 1 to 4 carbon atoms such as methyl, ethyl, n-propyl, iso-propyl, n-butyl, sec.-butyl and tert.-butyl), tetrahydrofurfuryl methacrylate and glycidyl methacrylate. Other methacrylate monomers include polyfunctional methacrylates which have two or more methacrylate moieties per molecule.

Polyfunctional methacrylates may be categorized in one of the following three categories; aliphatic, cycloaliphatic or aromatic polyfunctional methacrylates. By definition these cycloaliphatic or aromatic polyfunctional methacrylates have at least one cycloaliphatic hydrocarbyl moiety and/or at least one aromatic hydrocarbyl moiety per molecule. Such aliphatic polyfunctional methacrylates may be selected from among materials which may be characterized as diluents in dental materials. Such methacrylates include alkylene glycol dimethacrylates, polyalkylene glycol dimethacrylates and alkanetriol trimethacrylates. Thus, the polyfunctional aliphatic methacrylates may preferably contain 2 or 3 methacrylate groups per molecule. Also, these methacrylates may have a molecular weight between 198 and 400, preferably 374 or less or even 339 or less. Particular polyfunctional aliphatic methacrylates include ethylene glycol dimethacrylate, diethylene glycol dimethacrylate, triethylene glycol dimethacrylate, tetraethylene glycol dimethacrylate, pentaethylene glycol dimethacrylate, trimethylolpropane trimethacrylate, 1,6-hexanediol dimethacrylate, butanediol dimethacrylate (e.g., 1,4-butanediol dimethacrylate) and butanediol dimethacrylate (e.g., 2-butene-1,4-diol dimethacrylate). It is noted that the molecular weight of ethylene glycol dimethacrylate is 198, the molecular weight of trimethylolpropane trimethacrylate is 339 and the molecular weight of pentaethylene glycol dimethacrylate is 374.

Preferred cycloaliphatic or aromatic polyfunctional methacrylates include those which are known to be suitable for use in certain dental materials, particularly composite restorative materials. Examples of such cycloaliphatic and aromatic polyfunctional methacrylates are given in the following U.S. Pat. Nos. 3,066,112 (Bowen); 3,179,623 (Bowen); 3,194,783 (Bowen); 3,194,784 (Bowen); 3,539,533 (Lee II et al); 3,541,068 (Taylor); 3,597,389 (Taylor); 3,629,187 (Waller); 3,721,644 (Stoffey et al); 3,730,947 (Stoffey et al); 3,751,399 (Lee, Jr., et al); 3,766,132 (Lee, Jr., et al); 3,774,305 (Stoffey et al); 3,860,556 (Taylor); 3,862,920 (Foster et al); 3,926,906 (Lee II et al); 4,102,856 (Lee, Jr.); 4,107,845 (Lee, Jr., et al); and 4,131,729 (Schmitt et al). Further general information on polymer based dental materials is given on pages 501–508 and 515–517 of the *Kirk-Othmer Encyclopedia of Chemical Technology*, Third Edition, Volume 7 (1979). The entire disclosure of the patents and the Kirk-Othmer reference set forth in this paragraph are hereby incorporated by reference and relied upon.

Cycloaliphatic or aromatic polyfunctional methacrylates suitable for use in the preferred adhesives of the present invention preferably have 2–4 methacrylate moieties per molecule, most especially exactly two methacrylate moieties per molecule. Examples of polyfunctional methacrylates having three or four methacrylate moieties are given in the Stoffey et al U.S. Pat. No. 3,721,644. An example of a methacrylate having four methacrylate moieties per molecule is represented in the above-mentioned Stoffey et al patent by the formula:

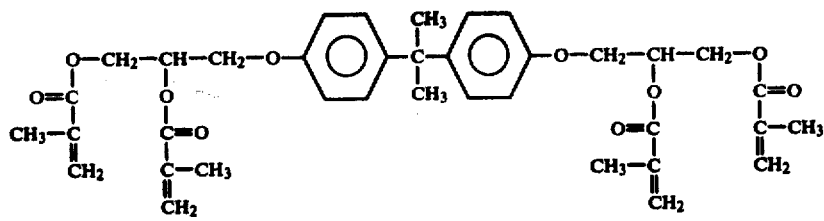

This methacrylate has a molecular weight of 648. Thus, cycloaliphatic or aromatic polyfunctional methacrylates suitable for use in the adhesives of the present invention may have a molecular weight of at least 648. Furthermore, even higher molecular weight polyfunctional cycloaliphatic or aromatic methacrylates may be used. For instance, in the Waller U.S. Pat. No. 3,629,187 there is mentioned a dimethacrylate adduct of dodecyl isocyanate with Bis-GMA, i.e., the adduct of dodecyl isocyanate with 2,2-bis[4'(3"-methacroyl-2"-hydroxypropoxy)phenyl]propane. Such an adduct may be represented by the formula:

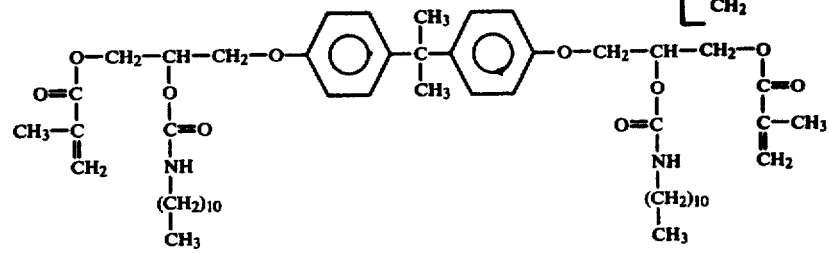

This adduct has a molecular weight of 904.

Other polyfunctional cycloaliphatic or aromatic polyfunctional methacrylates include those of the following formulae:

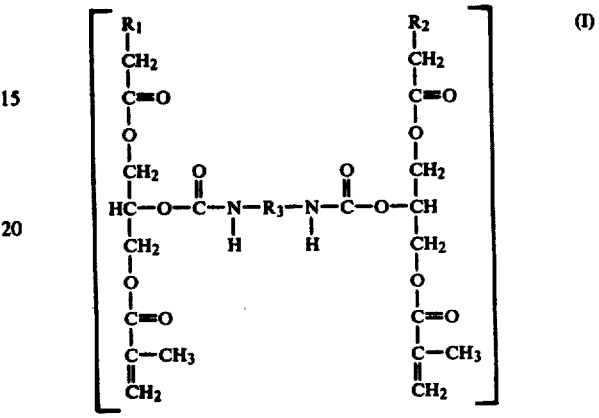

where
R₁ and R₂ may be the same or different and are cyclohexyl or phenyl groups which may be substituted or unsubstituted; and
R₃ is an aliphatic cycloaliphatic or aromatic group having 6 to 14 carbon atoms; and

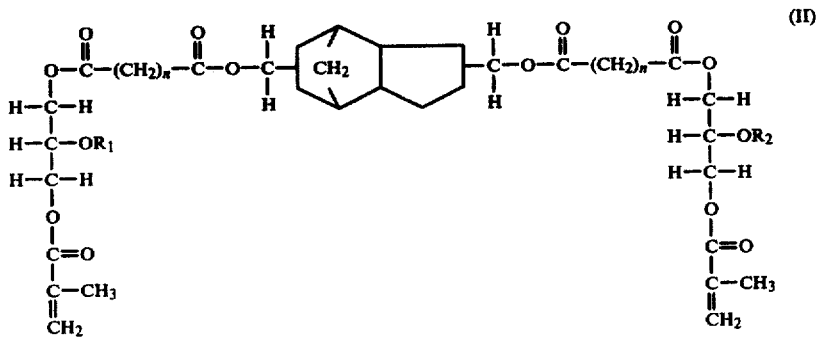

where
n represents a number of 2 to 8;
R₁ and R₂ are the same or different and are hydrogen groups of the formula:

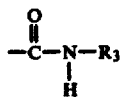

where $R_3$ is an aliphatic, aromatic or cycloaliphatic group having 1 to 14 carbon atoms.

Preferred cycloaliphatic or aromatic polyfunctional methacrylates suitable for use in the adhesives of the present invention include 2,2-bis[4'(3"-methacroyl-2"-hydroxypropoxy)phenyl]propane, 2,2-bis[4'(2"-methacroylethoxy)phenyl]propane, 2-methacroylethyl-3-methacroyl-2-hydroxypropyl tetrahydrophthalate, 2-methacroylethyl-3-methacroyl-2-hydroxypropyl hexahydrophthalate, 2,2-bis(4'-methacroylpheny)propane, 1,4-bis(methacroylmethyl) benzene and 1,4-bis(methacroylmethyl) cyclohexane.

In view of the foregoing examples of cycloaliphatic or aromatic polyfunctional methacrylates, it can be seen that these methacrylates may contain one or more monovalent or multivalent (e.g., di- or trivalent) aliphatic hydrocarbyl moieties covalently linked to the remaining moieties of the molecule. Such aliphatic moieties may have 1–14 carbon atoms and include, e.g., those of the following formulae:

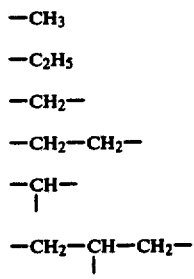

Further examples of such moieties are readily apparent with reference to the specific polyfunctional cycloaliphatic or aromatic methacrylates mentioned herein. Thus, it will further be understood that the polyfunctional cycloaliphatic or aromatic methacrylates may contain either oxygen or both oxygen and nitrogen in alcohol moieties (—OH), ether moieties (—O—) or carbamoyl moieties

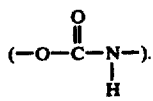

Cycloaliphatic or aromatic polyfunctional methacrylates suitable for use in the preferred adhesives of the present invention may have a molecular weight of 270 or more, preferably from 274 to 904.

The preferred adhesive components of the present invention may comprise 40% by weight or more of the polyfunctional methacrylates, preferably 40–90% by weight, 60–90% by weight or even 80–85% by weight. The quantities of aliphatic polyfunctional methacrylates and cycloaliphatic or aromatic polyfunctional methacrylates may be expressed in terms of the weight of the polyfunctional methacrylates or in terms of the total weight of the adhesive component. Based upon the weight of the polyfunctional methacrylates, the aliphatic polyfunctional methacrylates may constitute 10–80% by weight, preferably 20–30% by weight, and the cycloaliphatic or aromatic polyfunctional methacrylates may constitute 20–100% by weight, preferably 70–80% by weight. Based upon the total weight of the adhesive components, the aliphatic polyfunctional methacrylates may constitute from 0% to about 70% by weight, preferably from about 10% to about 30% by weight, and the cycloaliphatic or aromatic methacrylates may constitute from about 8% to about 90% by weight, preferably from about 45% to about 65% by weight. The cycloaliphatic or aromatic polyfunctional methacrylates are preferably present in excess of the aliphatic polyfunctional methacrylates, more preferably in a ratio of at least about 1.5:1 and most preferably from about 3:1 to about 4:1.

Although the above-mentioned polyfunctional methacrylates preferably constitute all or essentially all of the polymerizable monomers in the adhesive components, it is also possible to include small amounts, e.g., up to about 10% by weight of the adhesive component, of monofunctional methacrylic monomers. However, it is noted that due to the objectionable odor and properties of methacrylic acid, this monomer should not be present in excess of about 2% by weight based upon the weight of the adhesive.

Acrylic monomers, such as the acrylic analogues of the monofunctional or polyfunctional methacrylates mentioned herein (e.g., methyl acrylate or ethylene glycol diacrylate) may be used in small quantities, e.g., up to about 10% by weight based upon the weight of the adhesive component, but these acrylic monomers are preferably not included in the adhesive components.

In methacrylic based dental adhesives, it has been surprisingly found that the presence of one or more polymers containing at least one butadiene or substituted butadiene moiety improved dramatically the retention of pontics bonded with such adhesive to the abutment teeth. Such adhesive, in addition to improved flexibility and fatigue resistance, shows an outstanding impact resistance and resilience.

The polymers containing at least one butadiene or substituted butadiene moiety may be characterized as polymers of one or more conjugated diene monomers, preferably containing 4 to 10 carbon atoms. Copolymers of such monomers are also contemplated within the meaning of polymers containing at least one butadiene or substituted butadiene moiety.

Since the conjugated diene monomers may be unsubstituted or substituted with hydrocarbons, these monomers may in some instances be characterized as hydrocarbons. However, other substituents are possible, such as chlorine. Thus, the conjugated diene monomers containing chlorine may be characterized as chlorinated hydrocarbons, e.g., chloroprene. Particular examples of conjugated diene monomers include 1,3-butadiene, isoprene, chloroprene, 1,3-pentadiene and 2,3-dimethyl-1,3-butadiene.

As mentioned previously the elastomer may be a homopolymer of the conjugated diene monomer of a copolymer thereof. Suitable comonomers include alkylene monomers having from 2 to 10 carbon atoms. Particular comonomers include styrene, acrylonitrile, methacrylonitrile, lower alkyl acrylate, lower alkyl methacrylate, and monounsaturated lower alkyl hydrocarbons. Such lower alkyl groups include hydrocarbyl groups having 1 to 4 carbon atoms such as methyl, ethyl, n-propyl, iso-propyl, n-butyl, sec-butyl and tert-butyl.

Particular polymers containing at least one butadiene or substituted butadiene moiety include polybutadiene, polyisoprene, polychloroprene, styrene-butadiene, acrylonitrile-butadiene, acrylonitrile-butadiene-styrene, and methylmethacrylate-butadiene-styrene. These polymers preferably constitute elastomers which are characterized by high impact strength.

Certain of these elastomers are also known as: SBR (styrene-butadiene); PBR or BR (polybutadiene); neoprene (polychloroprene); nitrile or NBR (acrylonitrile-butadiene); ABS (acrylonitrile-butadiene-styrene); and MBS (methacrylonitrile-butadiene-styrene).

The elastomers may be made from a variety of monomers in various proportions. For instance, in the case of polybutadiene, polyisoprene or polychloroprene, respectively, the elastomer may be formed entirely from a single conjugated diene monomer. It is further noted that SBR may be made from about 20-25% styrene, and nitrile rubber may be made from 25-45% acrylonitrile. The proportions of monomeric moieties in ABS or MBS may vary depending upon the manner in which these elastomers are made. For example, ABS may contain approximately, e.g., 24% acrylonitrile, 33% butadiene and 43% styrene moieties, but other monomeric proportions are possible. Preferably, however, the butadiene moieties should comprise at least 20% of the monomeric moieties of the elastomer and most especially at least 30% of these moieties.

Molecular weight of the elastomers is not believed to be a critical parameter in selecting suitable polymeric elastomers of the types specified. Accordingly, selection of molecular weight is deemed to be a matter of choice. Obviously factors, such as the solubility of the elastomer in the liquid portion of the adhesive and the effect of the elastomer on the consistency of the uncured adhesive, may be related to the molecular weight of the elastomer, but selection of molecular weight in these respects is well within the skill of the art based upon routine experimentation.

Preferably, the butadiene or butadiene derivate containing polymer is present in the adhesive in the form of a colloidal or sub-micron sized dispersion. This dispersion may be achieved, e.g., by subjecting the polymeric elastomer to a high shearing force in the presence of the liquid components of the adhesive by means of a blender. This technique is particularly effective in the case of MBS elastomers. Such elastomers are often in the form of coarse particles of graft copolymers prepared by polymerizing a mixture of styrene and methylmethacrylate monomers in the presence of particles of either a styrene-butadiene copolymer or a latex of polybutadiene. Although not wishing to be limited to any particular theory or mechanism, it is possible that, when coarse particles of MBS are mixed with liquid methacrylate monomers in a blender, the graft, styrene-methylmethacrylate portion of the elastomer is dissolved, leaving behind an insoluble dispersion of fine polybutadiene or butadiene-styrene particles. A similar phenomenon has been described with respect to the partial dissolution of ABS or MBS in acrylonitrile monomer in the Gleave U.S. Pat. No. 4,102,945 (note particularly column 4, lines 21-27), the entire disclosure of which is incorporated herein by reference and relied upon.

The butadiene or butadiene derivative containing elastomer generally constitutes from about 2.5% to about 30% by weight of the preferred adhesive, preferably from about 10% to about 25% by weight.

The methacrylate resin used in the formulation of the invention should contain monomers that in the cured form exhibit low water sorption and high resistance to hydrolysis. Preferably, at least 10% of such resin should represent methacrylate monomers having no less than two methacrylate groups per molecule. Fillers or thickeners may be incorporated in the formulation in order to reduce polymerization shrinkage and the exothermic effect of polymerization or to achieve a desirable consistency.

The adhesive may be cured by an suitable means, a chemically initiated system being preferred. This initiating system involves the use of a catalyst or initiator plus an activator or accelerator. Peroxide catalysts such as benzoyl peroxide and tertiary amine accelerators such as N,N-bis(2-hydroxyethyl)-p-toluidine are preferred.

Dental adhesives may be fillerless or may contain one or more filler materials. These fillers are solid materials which are basically insoluble in the monomers of the adhesive components and which reinforce the polymeric matrix of the cured adhesive. These fillers may be inorganic or organic particles having an average particle size of 200 microns or less, preferably 40 microns or less or even 10 microns or less. For instance, particle sizes may range from about 1 to about 30 microns. Inorganic fillers are preferred and include materials such as fumed silica, precipitated silica, amorphous silica, crystalline silica, quartz, glass, calcium silicate, calcium phosphate, alumina and zeolites. Organic fillers include materials such as cross-linked polyalkylmethacrylates (e.g. polymethylmethacrylate cross-linked with ethylene glycol dimethacrylate), nylons (e.g., powdered nylon 66) and polyurethanes. These organic fillers are characterized in that they do not dissolve to any appreciable extent in the monomers of the adhesive component. It is noted that a polymethacrylate cross-linked with ethylene glycol dimethacrylate may swell without dissolving in these monomers. Fillers may preferably be present in an amount of 5-50% by weight, more preferably from about 10% to about 25% by weight, based upon the weight of the adhesive component.

Inorganic fillers may be treated with a coupling agent, such as an organosilane. Although such a treatment is optional, it is preferred for best results. These coupling agents are also sometimes referred to as finishing or keying agents and include materials such as [3-(methacroyl)propyl]trimethoxysilane. A sufficient coupling amount of such coupling agent may be a small amount such as from about 0.5 to about 1.0 part of coupling agent per 100 parts of filler. Methods for treating fillers with coupling agents are described, for example, in U.S. Pat. No. 3,066,112 (Bowen), wherein an aqueous solution of tris(2-methoxyethoxy)vinyl silane is catalyzed with sodium hydroxide to give a pH of 9.3 to 9.8, and the filler is treated with this solution, for example, one-half percent of silane per weight of fused quartz. A slurry so formed is dried at about 125° C. and cooled. Another technique for treating filler with a coupling agent is described in the passage extending from column 3, line 40 to column 4, line 4 of U.S. Pat. No. 3,862,920 (Foster et al).

Dental adhesives may also comprise a thickening amount of a thickening agent. Optionally, this thickening agent may be used in place of part or all of the filler content of the component. At least part and preferably all of the thickening agent is soluble in the monomers of the adhesive component, this soluble portion serving to thicken the adhesive component to the desired consistency. Thus, while both fillers and thickening agents may thicken the adhesive component, a substantial portion of the thickening agent is soluble in the monomers of the adhesive, whereas fillers are substantially insoluble in these monomers. Suitable thickening agents include polyalkylmethacrylates (e.g., lower alkylmethacrylate homopolymers such as a polymethylmethacrylate homopolymer) and copolymers of such alkylmethacrylates with one or more of monomers such as styrene, acrylonitrile, methacrylonitrile, lower alkyl acrylate, and monounsaturated lower alkyl hydrocarbons. These copolymers of alkymethacrylates comprise alkylmethacrylate as the predominant monomeric component. Thickening agents may be present in an amount of from about 0% to about 30% by weight, preferably less than 15% by weight, based upon the weight of the adhesive component.

Dental adhesives may include a stabilizing amount of one or more polymerization inhibitors, such as butylated hydroxytoluene (BHT) or hydroquinone methyl ether, to enhance the storage capacity of the uncured adhesive components. From about 0.05% to about 0.3% by weight of such inhibitor may represent a sufficient stabilizing amount.

Ultraviolet stabilizers such as 2-hydroxy-4-methoxybenzophenone (Cyasorb UV-9, a tradename of American Cyanamide) may be included to enhance the stability of the polymerizable materials as well as polymers resulting therefrom. For example, from about 0.4 to about 1.6% by weight of Cyasorb UV-9 based on the weight of the polymerizable materials may be used for this purpose.

Small quantities of other materials such as pigments (e.g., titanium dioxide) and plasticizers may also be included in the adhesive.

Dental adhesives may be packaged in any suitable manner. Preferably, a two-package system is used wherein one package comprises a peroxide-type polymerization initiator and the other package comprises a tertiary aromatic amine-type activator, the remaining components of the respective packages being essentially identical. However, other systems are also possible. For example, according to another two-package system, one package may contain both filler and catalyst and the other package may contain polymerizable material and accelerator. Another system involves packaging together each of the components excluding the catalyst component. When this system is used, polymerization can be initiated by introducing catalyst dropwise from a stock solution thereof. Such a stock solution is described in the Taylor U.S. Pat. No. 3,541,068 (note particularly column 6, lines 23-50).

Whatever packaging system is used, it is helpful to package polymerizable materials with one or more polymerization inhibitors such as BHT (e.g., 2,6-di-tert-butyl-p-cresol) in order to enhance storage life. Also, shelf life of components containing accelerators may be improved by removing traces of peroxides from these components with a reducing agent.

Desirably, when the adhesive is cured upon the admixture of components respectively containing initiator and accelerator, initial curing of the adhesive should take place in about 1 to about 2 minutes upon initial contacting of these components in order to permit adequate mixing and manipulation of these components outside the mouth. However, final curing is desirably delayed for 4 to 6 minutes from the initial contacting of the adhesive components in order to permit proper working of the adhesive and, e.g., adjustment of the pontic inside the mouth. Thus, the adhesive is preferably capable of fully curing within about 10 minutes. When the adhesive is used to adhere a pontic to abutment teeth, the pontic may be held in place with molding clay while curing takes place.

The preferred adhesive of this invention exhibits such a set of mechanical properties that the possibility of structural breaking of the cured adhesive in clinical use is not considered as a likely occurrence. With the possibility of failures in the material itself virtually eliminated, the improvement in adhesive strength to conditioned tooth enamel became of primary concern. Bonding strength to the pontic presented a lesser problem because it may be controlled and improved by proper mechanical preparations. Materials normally used as enamel conditioner-etching agent, 25-75% solutions of ortho-phosphoric acid, provided adhesion strength to human enamel ranging from 1000 to 1800 psi, depending on acid concentration, etching time and degree of tooth mineralization. Adhesive strength of this magnitude corresponds, with a 0.06 sq.in. bonding area, to the 60-108 pound force required to dislodge the pontic in anterior teeth. Such bonding strength is considered satisfactory for anterior pontics since expected biting force on the incisor is in the range of 25-55 pounds. On molars, however, a biting force in excess of 60 pounds may be routinely expected attaining, in some individuals, values above 130 pounds. The adhesive strength that would meet such requirements was impossible to achieve using phosphoric acid etchants. Surprisingly, however, a significant improvement in adhesive strength has been obtained by the inventors when phosphoric acid was replaced with diluted hydrochloric acid. The adhesive strength was thus raised to at least about 2000 psi, even as high as 2400 psi, showing little variance between different tooth specimens and less dependence on etching time. On molar teeth with a 0.10 sq.in. expected bonding area, 2000 psi adhesion strength corresponds to 200 pounds of force required to dislodge the pontic which exceeds the biting force in clinical situations. The concentration of the diluted hydrochloric acid etchant should preferably be from about 2% to about 15% HCl in aqueous solution, more preferably from about 6% to about 12%.

One of the unexpected advantages of utilizing diluted HCl as an etchant is the relative uniformity of adhesive strengths obtainable when the etchant is contacted with teeth for any period of time between about 30 seconds and about 300 seconds. On the other hand, the adhesive strength ultimately obtainable via a phosphoric acid etching technique is relatively dependent upon the duration of contact of the etchant with the tooth surface.

The flexibility, fatigue resistance, resilience and high bonding strength of the preferred adhesive system of this invention makes it also especially suitable for immobilizing injured or periodontically affected teeth and for stabilizing teeth in order to retain the results of orthodontic treatment.

The invention is now illustrated by the examples given below. It should be understood, however, that these examples are given only for better explanation of the nature of the invention without limiting, in any way, its scope that has been determined in claims.

EXAMPLE I

The adhesive material had the following chemical composition:

| PART A | | PART B |
|---|---|---|
| 66 | 2,2bis[4'(2"-methacroylethoxy)phenyl]-propane | 66 |
| 12 | 2,2bis[4'(3-methacroyl-2-hydroxy propoxy)-phenyl]propane | 12 |
| 22 | triethyleneglycol dimethacrylate | 22 |
| 22 | copolymer of methylmethacrylate, butadiene and styrene (Blendex 436 by Borg-Warner) | 22 |
| 0.1 | 2,6-di-tert-butyl-p-cresol | 0.1 |
| 10 | silica | 10 |
| 5 | N,N—bis(2-hydroxyethyl)-p-toluidine | — |
| — | benzoyl peroxide | 2 |
| — | titanium dioxide | 2 |

It is noted that the Blendex 436 by Borg-Warner was in the form of coarse particles of an MBS polymer. This polymer was believed to be made by polymerizing a mixture of styrene and methacrylate monomers in the presence of a latex of polybutadiene. The ratios of the components were believed to be such that impact strength of mixtures of the resulting polymer with polyvinyl chloride were maximized.

Parts A and B of the adhesive material had the consistency of a light paste. Parts A and B when mixed together in about equal amounts cured in 3 minutes at 23° C. The adhesive bond of this material to human teeth etched for 120 seconds with 50% O-phosphoric acid for two minutes measured under shear forces, was 800-1400 psi. On teeth etched for 30, 60, and 120 seconds with 9% hydrochloric acid solution, the adhesive strength measured on shear was in excess of 2000 psi. A specimen of cured adhesive exhibited outstanding impact resistance. Its diametral tensile strength was 3300 psi, diametral tensile modulus—316,000 psi and hardness (Barcol) —87.

EXAMPLE II

An acrylic denture tooth was roughened on both interproximal sides with a sandpaper disc and two 1 mm deep and 1.5 mm in diameter holes were drilled on each side. Two extracted human molar teeth were etched for 1 minute on the side to be bonded with 9% hydrochloric acid solution, then washed and dried. A mixture of equal amounts of Part A and B pastes described in Example I were prepared and applied over the etched area of teeth and over the roughened area of the pontic. The pontic was placed between the teeth and held in place with the help of a molding clay until the adhesive cured. The entire unit was immersed for two hours in 37° C. water, cast in a dental stone and the force required to dislodge the pontic was measured with steadily increasing load applied perpendicularly at the center of the pontic. The force required to dislodge the pontic was found in three consecutive samples to be in excess of 150 pounds.

The performance of the adhesive was also checked in clinical application on two males and two females. The adhesively bonded pontic replaced the second molar. No failure of the pontic was experienced in any of these cases.

All percentages expressed herein are by weight unless otherwise specified.

While certain aspects of the present invention have been described primarily with respect to the bonding of pontics to abutment teeth, it will be understood that these aspects may also be applied to other dental treatments such as the bonding of orthodontic brackets to tooth surfaces. Thus, while certain representative embodiments and details have been shown for the purpose of illustrating the invention, it will be apparent to those skilled in the art that various changes and modifications may be made therein without departing from the spirit or scope of the invention. It will further be understood that the invention may comprise, consist essentially of or consist of the steps or materials recited herein.

What is claimed is:

1. A method for adhesively mounting in the mouth a dental article which is a pontic or a fixed bridge of one or more pontic teeth by securing bonding surfaces on the article to be mounted in the mouth to support surfaces respectively of abutment teeth that are adjacent the mounting location of the article but at opposite sides of it respectively, comprising the steps of:
   (i) etching said support surfaces of said abutment teeth with a suitable chemical etchant;
   (ii) applying a curable dental adhesive to said bonding surfaces on said article and to said etched support surfaces of said abutment teeth; and
   (iii) contacting said bonding surfaces with said support surfaces, each surface containing said applied dental adhesive of step (ii), whereby said adhesive hardens to bond the dental article in place,
wherein said dental adhesive is a methacrylate based dental adhesive comprising from about 2.5% to about 30% by weight of an elastomer or a mixture of two or more of said elastomers, said elastomer or elastomers being selected from the group consisting of homopolymers and copolymers of at least one conjugated diene monomer containing 4 to 10 carbon atoms.

2. A method according to claim 1, wherein said etching step (i) comprises treating said support surfaces for 30-300 seconds with a B 2-15% solution of hydrochloric acid.

3. A method according to claim 1, wherein said conjugated diene monomers are hydrocarbons or chlorinated hydrocarbons.

4. A method according to claim 1, wherein said conjugated diene monomers of said adhesive are selected from the group consisting of 1,3-butadiene, isoprene, chloroprene, 1,3-pentadiene and 2,3-dimethyl-1,3-butadiene.

5. A method according to claim 1, wherein said copolymers of said adhesive are copolymers of at least one of said conjugated diene monomers with at least one alkylene monomer having from 2 to 10 carbon atoms.

6. A method according to claim 1, wherein said homopolymers or copolymers of said adhesive are selected from the group consisting of polybutadiene, polyisoprene, polychloroprene, styrene-butadiene, acrylonitrile-butadiene, acrylonitrile-butadiene-styrene, and methylmethacrylatebutadiene-styrene.

7. A method according to claim 1, wherein said adhesive comprises from about 40% to about 95% by weight of at least one methacrylic monomer.

8. A method according to claim 1, wherein said elastomer of said adhesive is at least partially undissolved in the liquid portion of the adhesive, the undissolved elastomer being present in the form of a colloidal or submicron sized dispersion.

9. A method according to claim 1, wherein said adhesive comprises from about 5% to about 50% by weight of inorganic filler.

10. A method according to claim 9, wherein said filler of said adhesive is selected from the group consisting of fumed silica, precipitated silica, amorphous silica, crystalline silica, quartz, glass, calcium silicate, calcium phosphate, alumina, zeolites, cross-linked polyalkylmethacrylates, polyurethanes and nylon.

11. A method according to claim 1, wherein said adhesive comprises at least 10% by weight of at least one polyfunctional methacrylate monomer.

12. A method according to claim 1, wherein said adhesive comprises two parts capable of curing upon mixing of these parts, one of said parts comprising a peroxide-type polymerization initiator and the other of said parts comprising a tertiary aromatic amine-type activator, and said method further comprises mixing together said parts prior to said application step (ii).

13. A method according to claim 1, wherein said adhesive comprises:
  (a) from about 45% to about 65% by weight of a cycloaliphatic or aromatic polyfunctional methacrylate or a mixture of two or more of said cycloaliphatic or aromatic polyfunctional methacrylates, said cycloaliphatic or aromatic polyfunctional methacrylate or methacrylates being selected from the group consisting of 2,2-bis[4'(3''-methacroyl-2''-hydroxypropoxy)phenyl]propane, 2,2-bis[4'(2''-methacroylethoxy)phenyl]propane, 2-methacroylethyl-3-methacroyl-2-hydroxypropyl tetrahydrophthalate, 2-methacroylethyl-3-methacroyl-2-hydroxypropyl hexahydrophthalate, 2,2-bis(4'methacroylphenyl)propane, 1,4-bis(methacroylmethyl)benzene and 1,4-bis (methacroylmethyl)cyclohexane;
  (b) from about 10% to about 30% by weight of an aliphatic polyfunctional methacrylate or a mixture of two or more of said aliphatic polyfunctional methacrylates, said aliphatic polyfunctional methacrylate or methacrylates being selected from the group consisting of ethylene glycol dimethacrylate, diethylene glycol dimethacrylate, triethylene glycol dimethacrylate, tetraethylene glycol dimethacrylate, pentaethylene glycol dimethacrylate, trimethylolpropane trimethacrylate, 1,6-hexanediol dimethacrylate, butane diol dimethacrylate, and butene diol dimethacrylate;
  (c) from about 10% to about 25% by weight of said elastomer or a mixture of said elastomers, said elastomer or elastomers being selected from the group consisting of polybutadiene, polyisoprene, polychloroprene, styrenebutadiene, acrylonitrile-butadiene, acrylonitrile-butadiene-styrene and methylmethacrylate-butadiene-styrene; and
  (d) from about 5% to about 15% by weight of an inorganic filler or a mixture of said fillers, said filler or fillers having an average particle size of 40 microns or less and being selected from the group consisting of fumed silica, precipitated silica, amorphous silica, crystalline silica, quartz, glass, calcium silicate, calcium phosphate, alumina, zeolites, cross-linked polyalkylmethacrylates, polyurethanes and nylons.

14. A method according to claim 13 wherein said etching step (i) comprises treating said support surfaces for 30-300 seconds with a 2-15% solution of hydrochloric acid.

15. A method according to claim 14 wherein the concentration of the hydrochloric acid is 6 to 12%.

16. A method according to claim 15 wherein (a) is a mixture of 2,2 bis[4'(2''-methacroylethoxy)phenyl]-propane and 2,2 bis[4'(3-methacroyl-2-hydroxypropoxy)-phenyl]propane, (b) is triethylene glycol dimethacrylate, (c) is a copolymer of methyl methacrylate, butadiene and styrene, and (d) is silica.

17. A method according to claim 14 wherein (a) is a mixture of 2,2 bis[4'(2''-methacroylethoxy)phenyl]-propane and 2,2 bis[4'(3-methacroyl-2-hydroxypropoxy)-phenyl]propane, (b) is triethylene glycol dimethacrylate, (c) is a copolymer of methyl methacrylate, butadiene and styrene, and (d) is silica.

18. A method according to claim 13 wherein (a) is a mixture of 2,2 bis[4'(2''-methacroylethoxy)phenyl]-propane and 2,2 bis[4'(3-methacroyl-2-hydroxypropoxy)-phenyl]propane, (b) is triethylene glycol dimethacrylate, (c) is a copolymer of methyl methacrylate, butadiene and styrene, and (d) is silica.

19. A method according to claim 2 wherein the concentration of the hydrochloric acid is 6 to 12%.

* * * * *